United States Patent [19]
Urbanowicz et al.

[11] Patent Number: 5,897,489
[45] Date of Patent: Apr. 27, 1999

[54] SNAP-ON SUCTION TUBE FOR LARYNGOSCOPE

[76] Inventors: Cynthia Urbanowicz, 117 Mayfair Dr., Pittsburgh, Pa. 15228; David Gallagher, 130 William Cir., McKees Rocks, Pa. 15136

[21] Appl. No.: 08/863,171

[22] Filed: May 27, 1997

[51] Int. Cl.⁶ ........................................... A61B 1/26
[52] U.S. Cl. .................................................. 600/185
[58] Field of Search ..................... 600/184, 185, 600/187, 190, 194, 197; 604/19, 27, 35

[56] References Cited

U.S. PATENT DOCUMENTS

| | | | |
|---|---|---|---|
| D. 271,135 | 10/1983 | Greenblatt | D24/17 |
| 2,854,004 | 9/1958 | Durrant | 600/187 X |
| 4,432,350 | 2/1984 | Breslau et al. | 600/187 |
| 4,832,004 | 5/1989 | Heckele . | |
| 4,878,486 | 11/1989 | Slater . | |
| 4,941,872 | 7/1990 | Felix et al. | 604/27 |
| 4,947,896 | 8/1990 | Bartlett . | |
| 5,063,908 | 11/1991 | Collins | 600/187 |
| 5,183,031 | 2/1993 | Rossoff . | |
| 5,217,465 | 6/1993 | Steppe | 604/27 X |
| 5,472,017 | 12/1995 | Kovalcheck . | |
| 5,551,946 | 9/1996 | Bullard | 600/187 X |

*Primary Examiner*—Jeffrey A. Smith
*Attorney, Agent, or Firm*—William L. Krayer

[57] ABSTRACT

A suction tube for use with a laryngoscope comprises a suction tube configured in the general profile of a laryngoscope, having an elongated clip which may be snapped on to the handle of a laryngoscope and easily removed after use. The device enables the user to work with the laryngoscope, the suction tube, and an airway tube all at the same time to accomplish oral intubation efficiently and without distractions.

10 Claims, 4 Drawing Sheets

SNAP-ON SUCTION TUBE FOR LARYNGOSCOPE

Technical Field

This invention relates to a suction device attachable to a laryngoscope, and particularly to the emergency application of suction to the airway to clear it to enable accurate and efficient oral intubation for the introduction of air or oxygen to patients in trauma.

BACKGROUND OF THE INVENTION

Patients suffering from serious medical emergencies as well as traumatic injuries such as facial or chest trauma frequently cannot breathe because their airway is blocked by blood, gastric contents, and other matter. They may be barely conscious or not conscious at all. Time is very limited for the emergency personnel on the scene, as oxygen deficiency in the blood begins almost as soon as breathing stops, and permanent damage to the brain will take place after three minutes.

Standard emergency practice for such patients heretofore has been to insert a laryngoscope, a lighted probe, into the mouth to push the tongue aside and search for the vocal cords as the insertion site or target for a plastic or other tube which can serve as an airway. The search is assisted by a suction probe which the user manipulates to remove the blocking materials. As soon as the vocal cords are seen, the attending emergency person inserts the relatively simple airway tube into the trachea between the vocal cords; the tube's outside end is typically connected to a positive pressure oxygen device. The airway tube usually is equipped with and passes through a balloon which seals the airway to prevent aspiration into the lungs of gastric contents and/or blood, which may continue to flow into and fill the throat area well after the airway passage is secured.

The laryngoscopic procedure is frequently performed under quite stressful conditions. Copious amounts of fluid flowing into the oropharynx is very common and frequently frustrates the efforts of emergency personnel to administer oral intubation. It is recommended that the most experienced person on the scene perform the procedure, which often must take place while the patient is undergoing other emergency treatment as well. Confusion and well-meant gestures from others often make it difficult for the person attempting the oral intubation to retain control of the process. A major cause of the difficulty of the procedure is that the laryngoscope is held in the left hand, while the right hand is occupied in manipulating the suction tube. As soon as a clear passage to the vocal cords is established, the suction tube must be removed and the airway tube picked up and moved to its place, i.e. inserted between the vocal cords, by the right hand, while the left hand still holds the tongue aside with the laryngoscope. During this maneuver, the blood and gastric matter commonly continues to flow into the airway, and the vocal cords disappear from view before the airway tube can be inserted. Delay is caused not just by the act of discarding the suction tube and picking up the airway tube, but also by the user having to glance away from the vital spot where the airway tube must be placed. Frequently when an opportunity is missed, further time is lost because it is determined that the patient must be ventilated with oxygen. The risk of aspiration of fluids into the lungs is extremely high at this point.

Standard and widely used laryngoscopes and suction tubes have not alleviated the problems described above; in fact, they exacerbate them in that the three articles handled by the user—the laryngoscope, the suction tube, and the airway tube—are completely separate and each requires the separate attention of the user.

Rosoff, in U.S. Pat. No. 5,183,031, combines a fiber optic light with a small suction channel, but does not provide for a blade, which is necessary to move the tongue away from the obstructed area.

Bartlett, in U.S. Pat. NO. 4,947,896, integrates the suction tube with the blade of the laryngoscope, i.e. it is entrained preferably in a service tube in the blade (col. 6, lines 4–6). This elaborate design is difficult to make and, because of the integration of the tube and the blade, means that the suction tube cannot economically be disposed of after use but must be sterilized along with the blade. Bartlett says the same tube can be used for either suction or "introduction of materials". He uses a channel alongside of the handle for guiding the tube (col. 6 line 45). Bartlett's main contribution to the art appears to be the "gull wing" shape of his blade.

A more or less standard appearance of a laryngoscope blade and handle assembly is shown in Greenblatt's U.S. Pat. No. Des 271,135. The present invention may be used with such a laryngoscope.

Slater, in U.S. Pat. No. 4,878,486, discloses a disposable sheath, sleeve or pocket-like device for covering the blade of a laryngoscope, and utilizes a ready source of vacuum to assure a tight fit of the sheath to the blade.

Suction is drawn directly through the blade and handle of a laryngoscope designed specifically for laser treatment of the larynx, in U.S. Pat. No,. 4,832,004 by Heckele et al. The passage is designed to remove gaseous materials rather than liquids.

None of the above devices satisfy the need for a convenient, easily manipulable way or device to clear the airway and insert an oxygen tube.

SUMMARY OF THE INVENTION

Our invention is a suction device which easily and instantly clamps onto a laryngoscope. It enables the user to move the tongue and clear the oropharynx easily and simply with one hand, leaving the other hand free to hold an airway tube for insertion immediately on clearing a passageway through the vocal cords. The distal end of the suction device is readily manipulated by a finger of the hand holding the laryngoscope. Optionally, suction may be applied by simply covering a hole in the suction device, which is connected to a remote source of vacuum. Other features and details of our invention will be explained with reference to the drawings.

DETAILED DESCRIPTION OF THE INVENTION

Figure 1:
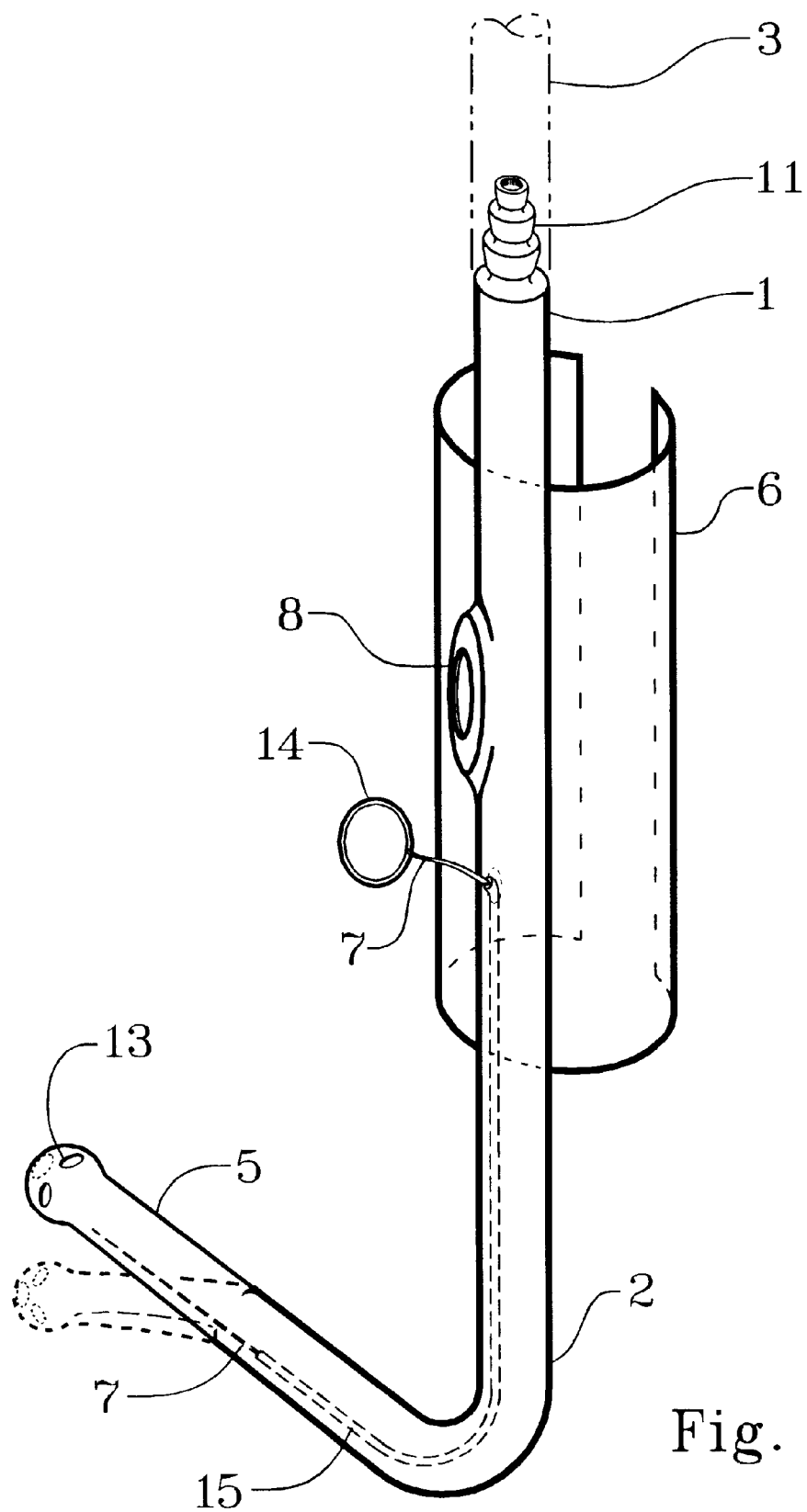
FIG. 1 is a perspective view of a preferred version of our basic suction device.

Referring now to FIG. 1, suction tube 1 has an elongated clip 6 firmly attached to suction tube 1. Preferably transparent suction tube 1 has a proximal end 11 adapted to attach to a vacuum source 3, and a flexible distal end 5. Suction tube 1 has an intake opening 13 at distal end 5 for taking in fluids and other matter, a suction control opening 8 for controlling the suction in suction tube 1, and a flexible tip manipulation cord 7 for manipulating the distal end 5 of the suction tube 1. Manipulation cord 7 has a ring 14 on its end for the insertion of a finger. Pulling on ring 14 will place tension on cord 7, which passes through a separate small diameter lumen or tube 15 preferably inside suction tube 1. Suction tube 1 includes a curve 2 of about 90° which is relatively stiff—that is, it is stiff enough to be maintained throughout normal usage so that the flexibility of flexible distal end 5 of suction tube 1 will be exerted from a point no further back on suction tube 1 than curve 2.

Figure 2A:
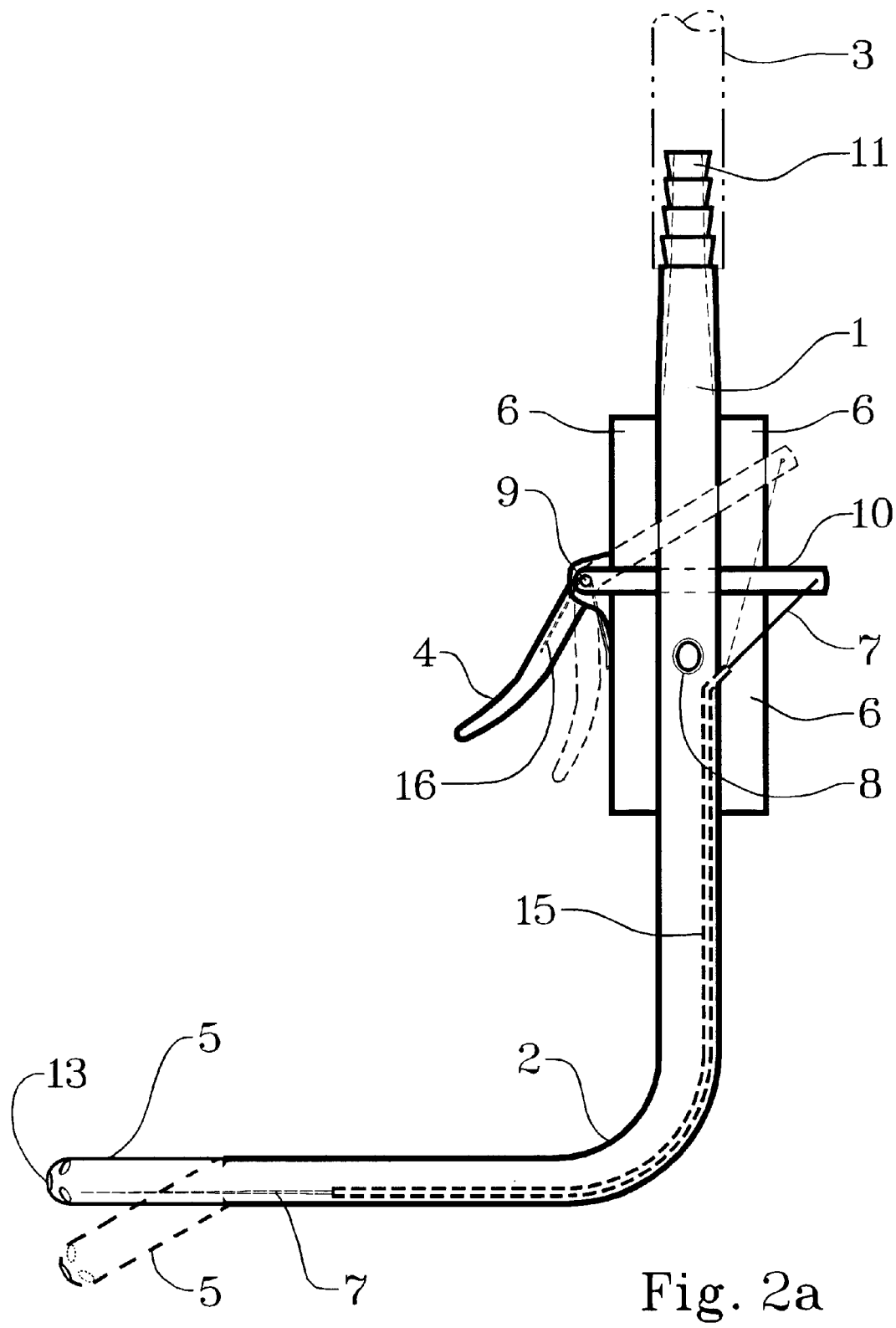
FIG. 2A shows another preferred variation of our device having a trigger for manipulating the distal end of the suction tube.

FIG. 2A shows a preferred version of the suction device. The suction tube 1 has an elongated clip 6 fixed to it as in FIG. 1, and in this case the flexible tip manipulation cord 7 is connected to arm 10 which is moved by trigger 4, mounted on pivot 9 generally near the center of elongated clip 6. Manipulation cord 7 may be retained next to suction tube 1 in any suitable manner; in this case it is held within a separate tube or lumen 15 of small diameter which is preferably fused or integrally molded or extruded inside suction tube 1. Generally V-shaped wire spring 16 is mounted on elongated clip 6 and on trigger 4 so it urges trigger 4 toward a tension-free attitude for manipulation cord 7. Thus, moving trigger 4 in a direction toward clip 6 will depress spring 16 and move distal end 5 of suction tube 1.

Figure 2B:
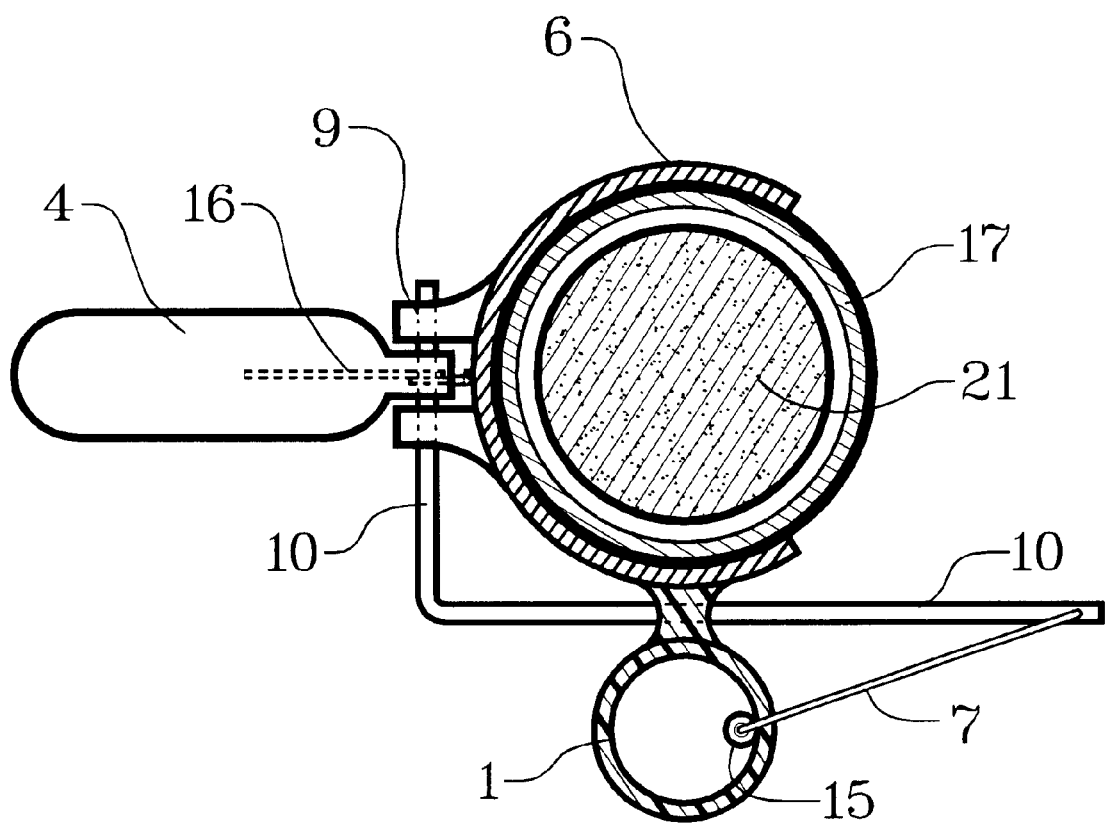
FIG. 2B is a section through the variation of FIG. 2A.

FIG. 2B is a cross section of the device near pivot 9 in FIG. 2A, as it is clipped on a laryngoscope 17. The section at this point is through a flashlight battery 21 inside laryngoscope 17; the battery 21 operates a light for the laryngoscope as is known in the art. The laryngoscope 17 is substantially surrounded by clip 6, which, is made of material resilient enough that it may be stretched open to close over the laryngoscope 17 and clamp firmly to it. Elongated clip 6 need not be transparent but is desirably made of the same material as the rest of suction tube 1 (which is transparent) if it is to be integrally molded or extruded. If the suction tube is designed for one-time usage and disposal, it need not be able to withstand autoclaving, but otherwise should be able to withstand it as is known in the art.

It will be seen that manipulation cord 7 is moved through lumen 15 by the movement of arm 10, which is controlled by trigger 4, in turn held in a normally relaxed or open position by spring 16.

Figure 3:
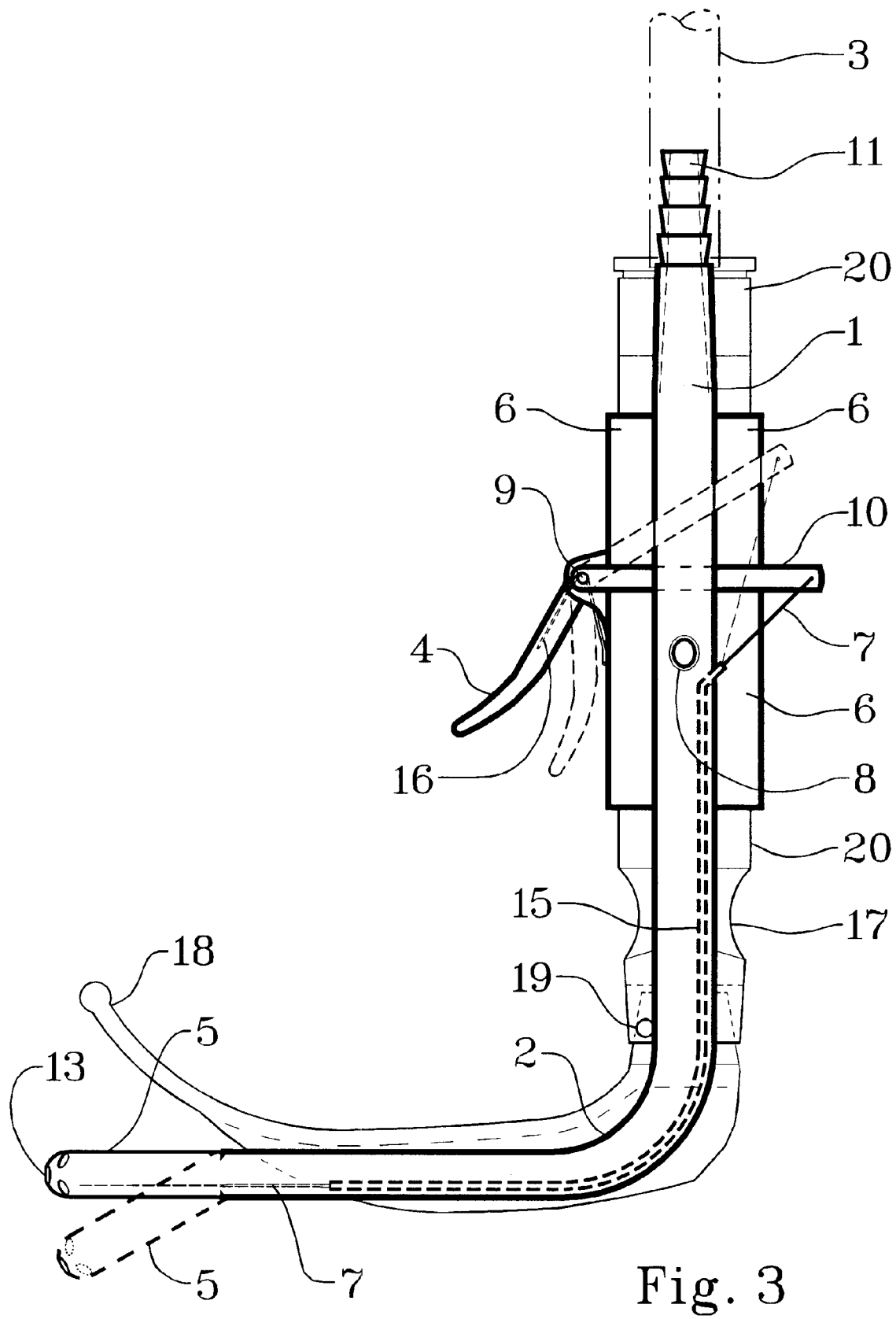
FIG. 3 is a side view of the suction device of FIG. 2A mounted on a laryngoscope.

In FIG. 3, our suction device has been clipped on to a laryngoscope. FIG. 3 is similar to FIG. 2A except that the laryngoscope is shown and the device is ready for use. The more or less conventional laryngoscope 17 comprises handle 20, joint 19, and probe 18, which carries a lamp not shown. Elongated clip 6 is seen to attach firmly to handle 20 so the user may work with both the laryngoscope 17 and the suction tube 1 simultaneously, using the left hand. While holding the assembled laryngoscope and suction device, the user can manipulate the patient's tongue with blade 18, maneuver the distal end 5 of suction tube 1, and turn the suction on or off by covering or uncovering suction control opening 8, all with the left hand. She or he can do so while holding an airway tube at the ready in the right hand, and insert it immediately, without the necessity for any distraction or other movements, as soon as the vocal cords are cleared and visible.

Persons skilled in the art will realize that our invention comprises broadly the assembly of a laryngoscope, a suction tube, and means for clipping them together. That is, any means for temporarily clipping or otherwise securing the suction device and laryngoscope together may be used. After use, the suction tube and laryngoscope may be handled differently for purposes of autoclaving or disposal.

We claim:

1. A suction device for attachment to a laryngoscope comprising a suction tube having a proximal end and a flexible distal end, means for manipulating said flexible distal end, and an elongated clip for temporarily fixing said suction device to a laryngoscope.

2. A suction device of claim 1 having an opening for directing suction to said flexible distal end of said suction tube.

3. A suction device of claim 1 wherein said means for manipulating said flexible distal end includes a trigger and arm mounted on a pivot.

4. A suction device of claim 1 wherein said means for manipulating said flexible distal end comprises a ring for insertion of a finger.

5. A suction device of claim 1 wherein said means for manipulating said flexible distal end of said suction tube includes a flexible cord.

6. A suction device of claim 5 including a suction control opening on said suction tube.

7. A suction device for attachment to a laryngoscope comprising a suction tube, said suction tube including a handle portion, an elongated resilient clip on said handle portion for clamping onto the handle portion of a laryngoscope, a substantially 90° curve, and a flexible distal end.

8. A suction device of claim 6 including means for manipulating said flexible distal end of said suction tube.

9. A suction device of claim 8 wherein said means for manipulating said flexible distal end of said suction tube include a flexible cord, a lumen for containing said flexible cord, and a lever for moving said flexible cord through said lumen.

10. A separable laryngoscope and suction assembly comprising a laryngoscope, a disposable suction tube having a distal end including an intake opening, and means for temporarily clipping said laryngoscope and said suction tube together.

* * * * *